United States Patent
Aichinger et al.

(10) Patent No.: US 6,518,452 B1
(45) Date of Patent: Feb. 11, 2003

(54) PROCESS FOR STABILIZING (METH) ACRYLIC ACID ESTERS AGAINST UNWANTED RADICAL POLYMERIZATION

(75) Inventors: Heinrich Aichinger, Mannheim; Holger Herbst, Frankenthal; Gerhard Nestler, Ludwigshafen, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/485,192

(22) PCT Filed: Jul. 23, 1998

(86) PCT No.: PCT/EP98/04631

§ 371 (c)(1),
(2), (4) Date: Feb. 7, 2000

(87) PCT Pub. No.: WO99/07664

PCT Pub. Date: Feb. 18, 1999

(30) Foreign Application Priority Data

Aug. 7, 1997 (DE) .......................... 197 34 171
Aug. 15, 1997 (DE) .......................... 197 35 223

(51) Int. Cl.$^7$ .............................. C07C 69/52
(52) U.S. Cl. ...................... 560/205; 562/598; 560/4
(58) Field of Search ...................... 560/205, 4; 562/598

(56) References Cited

U.S. PATENT DOCUMENTS

| 4,581,429 A | 4/1986 | Solomon et al. |
| 4,665,185 A | 5/1987 | Winter et al. |
| 4,670,131 A | 6/1987 | Ferrell et al. |
| 4,797,504 A * | 1/1989 | Roling .......................... 560/4 |
| 5,322,912 A | 6/1994 | Georges et al. |
| 5,322,960 A | 6/1994 | Sakamoto et al. |
| 5,412,047 A | 5/1995 | Georges et al. |
| 5,728,872 A | 3/1998 | Riemenschneider |

FOREIGN PATENT DOCUMENTS

| CA | 2087090 | 1/1992 |
| CA | 2211902 | 9/1996 |
| CN | 1052847 | 7/1991 |
| DE | 1 618 141 | 10/1970 |
| DE | 196 02 539 | 1/1996 |
| DE | 195 10 184 | 9/1996 |
| DE | 197 04 714 | 7/1997 |
| DE | 196 51 307 | 6/1998 |
| EP | 0 135 280 | 3/1985 |
| EP | 0 765 856 | 4/1997 |
| GB | 1064845 | 4/1967 |
| GB | 1127127 | 9/1968 |
| WO | WO 92/01665 | 2/1992 |
| WO | WO 98/25872 | 6/1998 |

* cited by examiner

Primary Examiner—Paul J. Killos
Assistant Examiner—Taylor V. Oh
(74) Attorney, Agent, or Firm—Oblon, Spivak, McClelland, Maier & Neustadt, P.C.

(57) ABSTRACT

A method is described of stabilizing (meth)acrylic esters against unwanted free-radical polymerization, in which the mixture to be stabilized has added to it a polymerization inhibitor mixture comprising at least one nitroxyl radical and/or at least one organic compound having at least one nitroso group, and at least one p-phenylenediamine.

5 Claims, No Drawings

PROCESS FOR STABILIZING (METH) ACRYLIC ACID ESTERS AGAINST UNWANTED RADICAL POLYMERIZATION

The present invention relates to a method of stabilizing esters of meth(acrylic) acid, which are present as a pure substance or as a constituent of mixtures which comprise no Brönsted acid (no protic acid) whose Brönsted acid strength is greater than the Brönsted acid strength of acrylic acid, against unwanted free-radical polymerization by adding a polymerization inhibitor comprising a p-phenylenediamine.

In this document (meth)acrylic acid is used as a shortened form of writing "acrylic acid and/or methacrylic acid".

Because of their activated vinyl group, esters of (meth)acrylic acid have a pronounced tendency to undergo free-radical polymerization. This is of advantage insofar as it makes (meth)acrylates outstandingly suitable for targeted preparation of polymers by the method of initiated free-radical polymerization, such polymers being required, for example, to produce adhesives. At the same time, however, the pronounced tendency to undergo free-radical polymerization is of disadvantage insofar as both the storage and the chemical and/or physical processing (for example, distillation or rectification) of the (meth)acrylates or of mixtures comprising such esters may, especially under the action of heat and/or light, be accompanied by unwanted, spontaneous free-radical polymerization of the (meth)acrylic esters. As well as the fact that such uncontrolled free-radical polymerizations of the (meth)acrylates or mixtures comprising them constitute a considerable hazard potential (the free-radical polymerization is highly exothermic and, consequently, in many cases explosive) they also have diverse other consequences. For example, polymer formed unintentionally during the distillation of mixtures comprising (meth)acrylic esters may deposit on the surface of the evaporator (where the high temperatures increase the propensity to form polymer), thereby undesirably reducing heat transfer. Alternatively, the polymer formed may clog the internals of rectification columns, causing unwanted pressure losses. Both phenomena necessitate the interruption of the rectification process for laborious removal of the polymer formed.

It is therefore common practice to add to these esters of (meth)acrylic acid and mixtures comprising such esters, in the course of both storage and chemical and/or physical processing, compounds which act as inhibitors of free-radical polymerization of the (meth)acrylates and hence stabilize them against unwanted free-radical polymerization.

From WO 92/01665 it is known to use as such an inhibitor a mixture of p-phenylenediamines with defined N,N-substitution. These p-phenylenediamines are said to be favorable polymerization inhibitors especially in the presence of strong acids. U.S. Pat. No. 4,797,504 recommends the use of p-phenylenediamines in combination with hydroxylamines as polymerization inhibitors for (meth)acrylic esters.

GB-A 1,064,845 contains the very general teaching to add organic compounds having a nitroso group, ie. an atomic grouping —N=O, as polymerization inhibitors to monomers having a vinyl group.

U.S. Pat. No. 5,322,960 discloses the addition to esters of (meth)acrylic acid of a polymerization-inhibiting mixture which includes, inter alia, a nitroxyl radical (a compound having at least one >N—O. group).

The teaching of JP-A 5/320217 is, inter alia, to stabilize (meth)acrylic acid against unwanted free-radical polymerization by adding a mixture that includes a nitroxyl radical and at least one polymerization inhibitor from the group consisting of phenothiazine, p-phenylenediamine, diphenylamine, hydroquinone and hydroquinone monomethyl ether. Such an inhibitor mixture is said also to reduce the tendency of (meth)acrylic acid to undergo polymerization in the course of its esterifications catalyzed by strong acids. JP-A 5/320217 also teaches that polymerization inhibitors suitable for reducing the polymerization tendency of (meth)acrylic acid are not necessarily appropriate for inhibiting the polymerization of their esters as well, which is supposed to be attributable to the fact that the ester no longer possesses the carboxyl group. Accordingly, JP-A 5/320217 contains no indication whatsoever that the inhibitor systems it recommends for (meth)acrylic acid might also be suitable for inhibiting the polymerization tendency of (meth)acrylic esters.

It is an object of the present invention, therefore, to provide a method of stabilizing esters of (meth)acrylic acid, which are present as a pure substance or as a constituent of mixtures which comprise no Brönsted acid whose Brönsted acid strength is greater than the Brönsted acid strength of acrylic acid, against unwanted free-radical polymerization by adding a polymerization inhibitor comprising a p-phenylenediamine, said process being more effective in inhibiting polymerization than the prior art processes acknowledged above.

We have found that this object is achieved by a method of stabilizing esters of (meth)acrylic acid, which are present as a pure substance or as a constituent of mixtures which comprise no Brönsted acid whose Brönsted acid strength is greater than the Brönsted acid strength of acrylic acid, against unwanted free-radical polymerization by adding a polymerization inhibitor comprising a p-phenylenediamine, which comprises adding to the pure substance or to the mixture a polymerization inhibitor which comprises:

a) at least one nitroxyl radical and/or at least one organic compound having at least one nitroso group (inhibitors a) and b) at least one p-phenylenediamine (inhibitors b).

A measure of Brönsted acid strength is the equilibrium constant (acid constant) of the reaction $HA + H_2O \rightleftharpoons A^\ominus + H_3O^\oplus$ at 25° C. and 1 atm, where HA is the Brönsted acid and $A^\ominus$ the associated conjugated base (cf. Christen, Grundlagen der allgemeinen und anorganischen Chemie, Verlag Sauerländer, Aarau, 1973, pp. 353/354).

Nitroxyl radicals (also known as N-oxyl radicals) suitable for the purposes of the invention are in particular those derived from a secondary amine that carries no hydrogens on the a carbons (in other words, the N-oxyl groups are derived from corresponding secondary amino groups). Particularly suitable among these are those N-oxyl radicals specified in EP-A 135280, prior application DE-A 19651307, U.S. Pat. Nos. 5,322,912, 5,412,047, 4,581,429, DE-A 1618141, CN-A 1052847, U.S. Pat. Nos. 4,670,131, 5,322,960, prior application DE-A 19602539, EP-A 765856 and JP-A 5/320217.

Examples of such suitable, stable N-oxyl radicals deriving from a secondary amine are those of the formula I

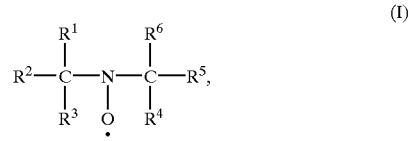

where $R^1, R^2, R^5$ and $R^6$=the same or different straight- or branched-chain, substituted or unsubstituted alkyls and $R^3$ and $R^4$=the same or different straight- or branched-chain, substituted or unsubstituted alkyls, or $R^3CNCR^4$=a substituted or unsubstituted cyclic structure.

Compounds I that are suitable in accordance with the invention are in particular those specified in EP-A 135 280, prior application DE-A 19651307, U.S. Pat. Nos. 5,322,912, 5,412,047, 4,581,429, DE-A 16 18 141, CN-A 1052847, U.S. Pat. Nos. 4,670,131, 5,322,960 and prior application DE-A 19602539.

Examples of these are those stable N-oxyl radicals of the formula I in which $R^1$, $R^2$, $R^5$ and $R^6$ are (identical or different) $C_1$–$C_4$-alkyls, such as methyl, ethyl, n-propyl, isopropyl, n-butyl, isobutyl or tert-butyl, linear or branched pentyls, phenyls or substituted derivatives thereof and $R^3$ and $R^4$ are (identical or different) $C_1$–$C_4$-alkyls, such as methyl, ethyl, n-propyl, isopropyl, n-butyl, isobutyl or tert-butyl, linear or branched pentyls, substituted derivatives thereof or, together with CNC, the cyclic structure

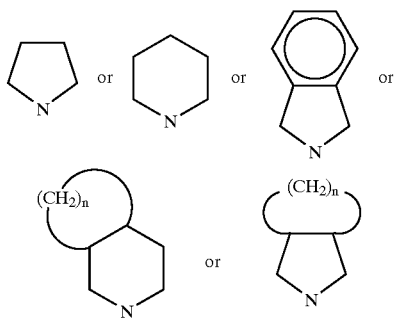

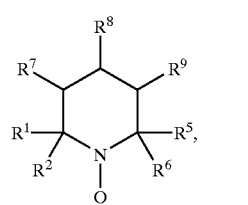

or

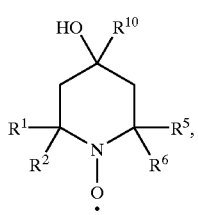

where n is an integer from 1 to 10 (frequently from 1 to 6), including substituted forms of such cyclic structures. Typical examples are 2,2,6,6-tetramethyl-1-oxyl-piperidine, 2,2,5,5-tetramethyl-1-oxyl-pyrrolidine and 4-oxo-2,2,6,6-tetramethyl-1-oxyl-piperidine.

The N-oxyl radicals I can be prepared by oxidizing the corresponding secondary amines using hydrogen peroxide, for example. They can generally be prepared as the pure substance.

N-oxyl radicals I suitable for the purposes of the invention include, in particular, piperidine or pyrrolidine N-oxyls and di-N-oxyls of the following formulae II to IX:

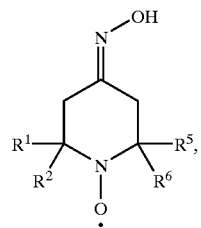 (II)

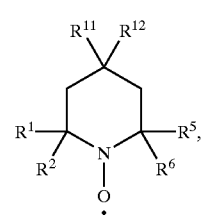 (III)

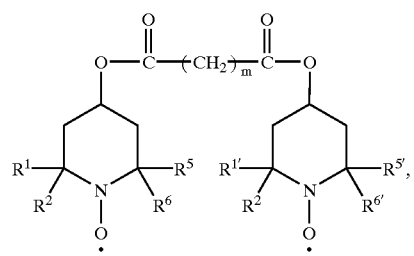 (IV)

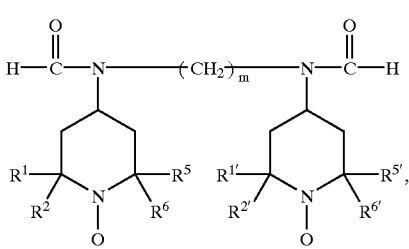 (V)

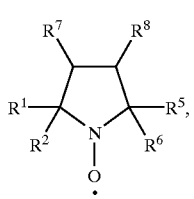 (VI)

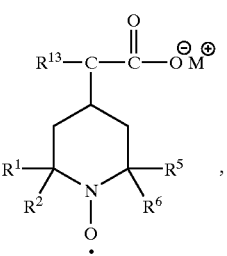 (VII)

(VIII)

(IX)

where m=from 2 to 10, $R^7, R^8, R^9$=independently of one another

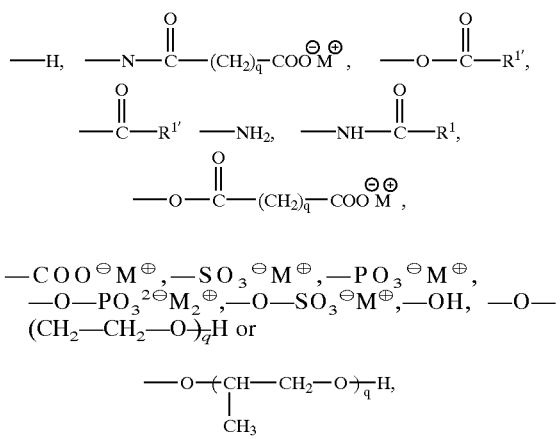

$-COO^\ominus M^\oplus, -SO_3^\ominus M^\oplus, -PO_3^\ominus M^\oplus,$
$-O-PO_3^{2\ominus}M_2^\oplus, -O-SO_3^\ominus M^\oplus, -OH, -O-$
$(CH_2-CH_2-O)_q H$ or

$M^\oplus$=a hydrogen or alkali metal ion,
q=an integer from 1 to 10,
$R^{1'}, R^{2'}, R^{5'}, R^{6'}$=independently of one another and independently of $R^1, R^2, R^5$ and $R^6$ the same groups as $R^1$,
$R^{10}=C_1-C_4$-alkyl, $-CH=CH_2, -CH\equiv CH, -CN,$

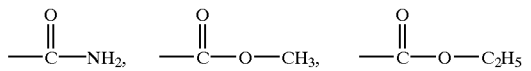

$-COO^\ominus M^\oplus, -COOCH_3$ or $-COOC_2H_5$,
$R^{11}$=an organic radical having at least one primary, secondary (eg. $-NHR^1$) or tertiary amino group (eg.— $NR^1R^2$) or at least one ammonium group $-N^\oplus R^{14}R^{15}R^{16}X^\ominus$ where $X^\ominus=F^\ominus, Cl^\ominus, Br^\ominus, HSO_4^\ominus,$ $SO_4^{2\ominus}, H_2PO_4^\ominus, HPO_4^{2\ominus}$ or $PO_4^{3\ominus}$ and $R^{14}, R^{15}$ and $R^{16}$ are mutually independent organic radicals (for example, independently of one another and independently of $R^1$, the same groups as $R^1$),
$R^{12}$=independently of $R^{11}$, the same groups as $R^{11}$ or $-H, -OH, C_1-C_4$-alkyl, $-COO^\ominus M^\oplus, -C\equiv CH,$

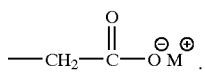

or hydroxy-substituted $C_1-C_4$-alkyl (for example hydroxyethyl or hydroxypropyl) or
$R^{11}, R^{12}$=together the oxygen of a carbonyl group, and
$R^{13}$=—H, —$CH_3$ or $-CH_2-\overset{O}{\underset{\|}{C}}-O^\ominus M^\oplus$.

Preferably, $R^1=R^2=R^5=R^6=R^{1'}=R^{2'}=R^{5'}=R^{6'}=-CH_3$.
Typical examples of N-oxyl radicals suitable in accordance with the invention are
4-hydroxy-2,2,6,6-tetramethyl-1-oxyl-piperidine,
4-hydroxy-2,6-diphenyl-2,6-dimethyl-1-oxyl-piperidine,
4-carboxy-2,2,6,6-tetramethyl-1-oxyl-piperidine,
4-carboxy-2,6-diphenyl-2,6-dimethyl-1-oxyl-piperidine,
3-carboxy-2,2,5,5-tetramethyl-1-oxyl-pyrrolidine,
3-carboxy-2,5-diphenyl-2,5-dimethyl-1-oxyl-pyrrolidine,
4-acetyl-2,2,6,6-tetramethyl-1-oxyl-piperidine, N,N'-bis(1-oxyl-2,2,6,6-tetramethylpiperidin-4-yl)-N,N'-bis formyl-1,6-diaminohexane and
bis(1-oxyl-2,2,6,6-tetramethylpiperidin-4-yl) adipate.

The preparation of
3-carboxy-2,2,5,5-tetramethyl-1-oxyl-pyrrolidine, for example, is given in Romanelli, M.; Ottaviani, M. F.; Martini, G.; Kevan, L., JPCH: J. Phys. Chem., EN, 93, 1, 1989, pp. 317–322.

The compounds (VI) and (VII) can be obtained as per U.S. Pat. No. 4665185 (eg. Ex. 7) and DE-A 19510184.

Other suitable examples are:

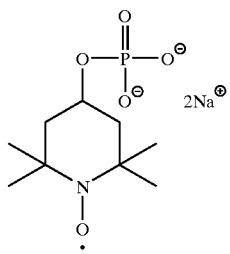

Sunamoto, Junzo; Akiyoshi, Kuzunari; Kihara, Tetsuji; Endo, Masayuki, BCS JA 8, Bull. Chem. Soc. Jpn., EN, 65, 4, 1992, pp. 1041–1046;

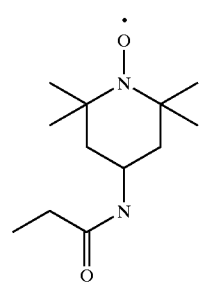

Beilstein Registry Number 6926369 $(C_{11}H_{22}N_3O_2)$;

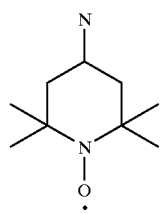

Beilstein Registry Number 6498805 (4-Amino-2,2,6,6-tetramethyl-1-oxyl-piperidine);

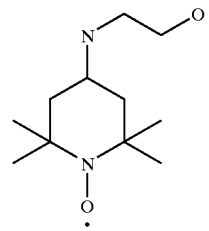

Beilstein Registry Number 6800244 $(C_{11}H_{23}N_2O_2)$;

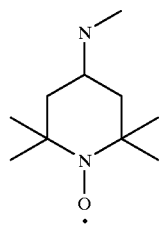

Beilstein Registry Number 5730772 (N-Methyl-4-amino-2,2,6,6-tetramethyl-1-oxyl-piperidine;

-continued

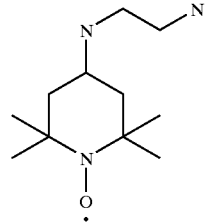
Beilstein Registry Number 5507538 (2,2,6,6-Tetramethyl-4-(2-aminoethyl amino)-1-oxyl-piperidine);

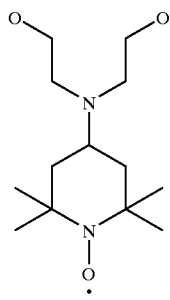
Beilstein Registry Number 4417950 (4<Bis(2-hydroxy-ethyl)>-amino-2,2,6,6-tetramethyl-1-oxyl-piperdine);

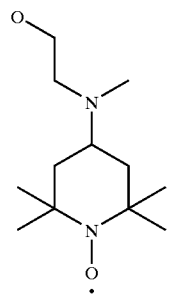
Beilstein Registry Number 4396625 ($C_{12}H_{25}N_2O_2$);

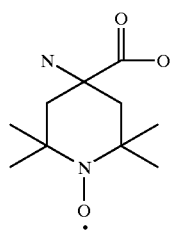
Beilstein Registry Number 4139900 (4-Amino-2,2,6,6-tetramethyl-4-carboxy-1-oxyl-piperidine);

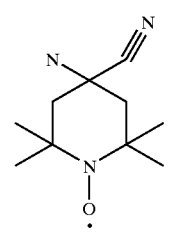
Beilstein Registry Number 4137088 (4-Amino-4-cyano-2,2,6,6-tetramethyl-1-oxyl-piperidine);

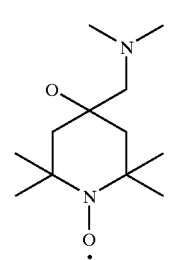
Beilstein Registry Number 3942714 ($C_{12}H_{25}N_2O_2$);

-continued

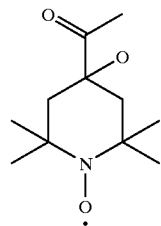
Beilstein Registry Number 1468515 (2,2,6,6-Tetramethyl-4-hydroxy-4-acetyl-1-oxyl-piperidine);

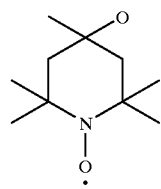
Beilstein Registry Number 1423410 (2,2,4,6,6-Penta-methyl-4-hydroxy-1-oxyl-piperidine);

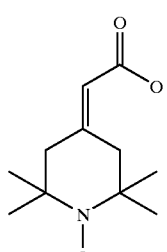
Beilstein Registry Number 6205316 (4-Carboxymethylene-2,2,6,6-tetramethyl-1-oxyl-piperidine);

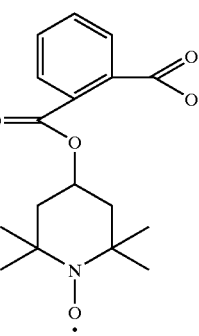
Beilstein Registry Number 1395538 (4-<2-Carboxy-benzoyloxy>-2,2,6,6-tetramethyl-1-oxyl-piperidine);

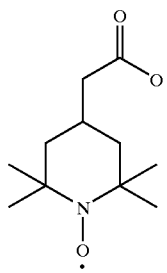
Beilstein Registry Number 3546230 (4-Carboxymethyl-2,2,6,6-tetramethyl-1-oxyl-piperidine);

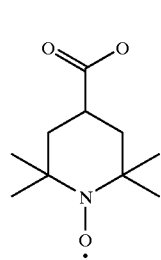
Beilstein Registry Number 3949026 (4-Carboxyl-2,2,6,6-tetramethyl-1-oxyl-piperidine);

-continued

| | |
|---|---|
| 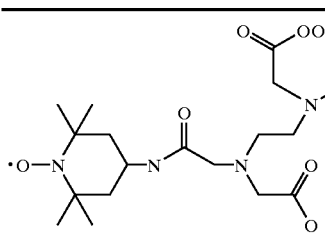 | Beilstein Registry Number 4611003 (Ethylenediaminetetra-acetic acid mono(1-oxy-2,2,6,6-tetra-methylpiperidin-4-yl amide); |
| 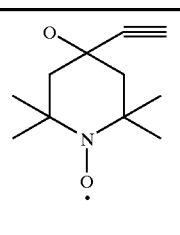 | Beilstein Registry Number 5961636 ($C_{13}H_{21}N_2O_4$) |
| 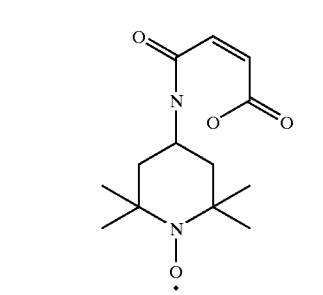 | Beilstein Registry Number 5592232 ($C_{15}H_{27}N_2O_4$); |
| 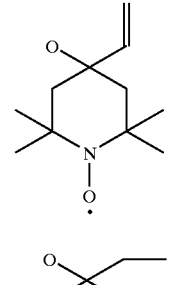 | Beilstein Registry Number 5080576 (Succinic acid N-(2,2,6,6-tetramethyl-1-oxyl-4-piperidinyl) monoamide); |
| 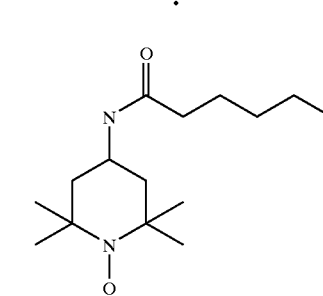 | Beilstein Registry Number 5051814 (4-(4-Hydroxybutan-oylamino)-2,2,6,6-tetramethyl-1-oxyl-piperidine); |
| 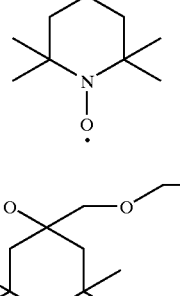 | Beilstein Registry Number 4677496 (2,2,6,6-Tetramethyl-4-oximino-1-oxyl-piperidine); |

-continued

| | |
|---|---|
| 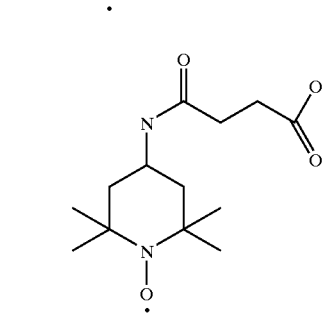 | Beilstein Registry Number 1451068 ($C_{11}H_{18}NO_2$); |
| 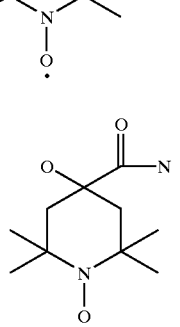 | Beilstein Registry Number 1451075 ($C_{11}H_{20}NO_2$); |
| 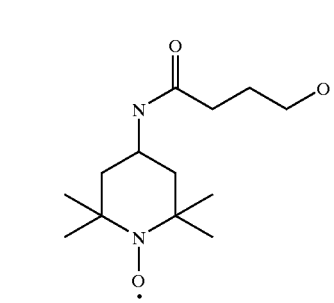 | Beilstein Registry Number 1423698 (4-Ethyl-4-hydroxy-2,2,6,6-tetramethyl-1-oxyl-piperidine); |
| 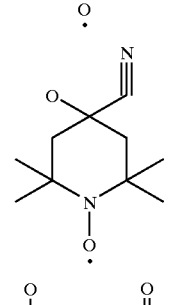 | Beilstein Registry Number 5509793 (4-Ethoxymethyl-4-hydroxy-2,2,6,6-tetramethyl-1-oxyl-piperidine); |
| 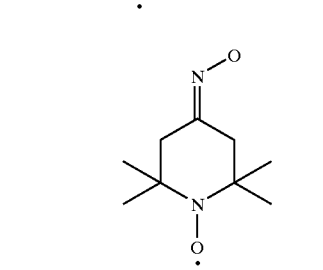 | Beilstein Registry Number 3960373 ($C_{10}H_{19}N_2O_3$); |
| | Beilstein Registry Number ($C_{10}H_{17}N_2O_2$); |
| 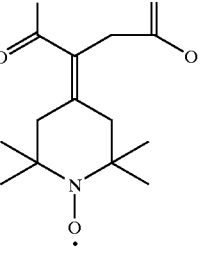 | Beilstein Registry Number 3985130 (2,2,6,6-Tetramethyl-1-oxyl-4-piperidylidene)-succinic acid); |

Other suitable examples are:

In accordance with the invention it is of course also possible to use mixtures of N-oxyl radicals.

Examples of organic nitroso compounds suitable in accordance with the invention are N-nitrosoarylamines or nitroso compounds where the nitroso group is attached directly to a carbon of an aromatic nucleus. Examples are nitrosophenols such as 4-nitrosophenol, nitrosonaphthols such as 2-nitroso-1-naphthol, nitrosobenzene, N-nitroso-N-methylurea, nitroso-N,N-dialkylanilines where alkyl=methyl, ethyl, propyl and/or butyl, N-nitrosodiphenylamine, N-nitrosophenylnaphthylamine, 4-nitrosodinaphthylamine and p-nitrosodiphenylamine. In accordance with the invention it is of course also possible to employ mixtures of these nitroso compounds.

p-Phenylenediamines suitable in accordance with the invention are those of the formula X

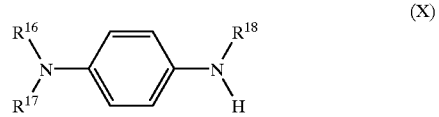

where $R^{16}$, $R^{17}$, $R^{18}$=independently of one another alkyl, aryl, alkaryl or aralkyl having up to 20 carbons, or hydrogen.

Particularly suitable compounds X are those where $R^{16}$, $R^{17}$, and $R^{18}$ are, independently of one another, methyl, ethyl, propyl, isopropyl, isobutyl, sec-butyl, n-butyl, pentyl, phenyl or naphthyl. Examples are N,N'-bis-sec-butyl-p-phenylenediamine,
N-phenyl-N'-isopropyl-phenylendiamine,
N-naphthyl-N'-sec-butyl-p-phenylenediamine,
N,N,N'-trimethyl-p-phenylenediamine, N,N,N'-triethyl-p-phenylenediamine, N,N-dimethyl-p-phenylenediamine,
N,N-diethyl-p-phenylenediamine,
N-phenyl-N',N'-dimethyl-p-phenylenediamine,
N-phenyl-N',N-diethyl-p-phenylenediamine,
N-phenyl-N',N'-dipropyl-p-phenylenediamine,
N-phenyl-N',N'-di-n-butyl-p-phenylenediamine,
N-phenyl-N',N'-di-sec-butyl-p-phenylenediamine,
N-phenyl-N'-methyl-N'-ethyl-p-phenylenediamine,
N-phenyl-N'-methyl-N'-propyl-p-phenylenediamine,
N-phenyl-N'-methyl-p-phenylenediamine,
N-phenyl-N'-ethyl-p-phenylenediamine,
N-phenyl-N'-propyl-p-phenylenediamine,
N-phenyl-N'-isopropyl-p-phenylenediamine,
N-phenyl-N'-butyl-p-phenylenediamine,
N-phenyl-N'-isobutyl-p-phenylenediamine,
N-phenyl-N'-sec-butyl-p-phenylenediamine,
N-phenyl-N'-tert-butyl-p-phenylenediamine,
N-phenyl-N'-n-pentyl-p-phenylenediamine,
N-phenyl-N'-n-hexyl-p-phenylenediamine,
N-phenyl-N'-(1-methylhexyl)-p-phenylenediamine,
N-phenyl-N'-(1,3-dimethylbutyl)-p-phenylenediamine,
N-phenyl-N'-(1,4-dimethylpentyl)-p-phenylenediamine and p-phenylenediamine. In accordance with the invention it is of course also possible to employ mixtures of p-phenylenediamines.

Suitable such mixtures are, in particular, those recommended in WO 92/01665.

The inhibitor mixture to be added in accordance with the invention judiciously comprises, based on the overall amount of inhibitors a) and inhibitors b) that is present therein, from 1 to 75% by weight of inhibitors a) and from 25 to 99% by weight of inhibitors b).

In other words, inhibitor mixtures to be added in accordance with the invention include those which, based on the overall amount of inhibitors a) and inhibitors b) that is present therein, comprise from 5 to 50% by weight (or from 5 to 25% by weight) of inhibitors a) and from 50 to 95% by weight (or from 75 to 95% by weight) of inhibitors b).

Based on the mixture comprising the esters to be stabilized, satisfactory stability is generally ensured by adding inhibitors a) and inhibitors b) in an overall concentration of from 10 to 5000 ppm by weight, often from 10 to 1000 ppm by weight. The latter is also valid for the customary temperatures of from 50 to 200° C., often from 60° C. to 160° C., at which (meth)acrylic esters are distilled.

(Meth)acrylic esters suitable for stabilization are, in particular, esters of (meth)acrylic acid with mono- or polyhydric alkanols, especially when these alkanols have 1 to 20 or 1 to 12 or 1 to 8 carbons. Typical examples of such esters are methyl, ethyl, n-butyl, isobutyl, tert-butyl and 2-ethylhexyl acrylate and methyl, ethyl, n-butyl and tert-butyl methacrylate.

The method of the invention is particularly suitable for stabilizing (meth)acrylic esters (especially the above typical examples) in the course of their distillative (or rectificative) separation from product mixtures as are present in the acid-catalyzed esterification of (meth)acrylic acid with alcohols, especial alkanols (especially $C_1$–$C_{12}$- or $C_1$–$C_8$-alkanols), following separation of the acid catalyst.

It is also suitable, however, for stabilizing mixtures which comprise these (meth)acrylic acids but which comprise neither a Brönsted acid whose Brönsted acid strength is greater than that of acrylic acid, nor acrylic or methacrylic acid itself. Such mixtures comprising (meth)acrylic esters are formed, for example, by the abovementioned mixtures of esterification products following the separation of the acid catalyst and following separation of the excess (meth)acrylic acid (whose removal from such mixtures generally leaves a (meth)acrylic acid content $\leq 1\%$ by weight, often $\leq 100$ ppm by weight and frequently $\leq 50$ ppm by weight, based on the mixture; in many cases, quantitative removal of the (meth) acrylic acid is possible).

Such acid-free esterification product mixtures generally contain from 80 to 95% by weight of (meth)acrylic esters, from 1 to 10% by weight of the alcohol employed for esterification, any organic solvent employed for the esterification, and small amounts of by products with a boiling point higher or lower than that of the (meth)acrylic ester (for example, water, ethers or Michael adducts). The water content is typically from 0.5 to 3% by weight, based on the mixture of esterification products.

The inhibitor mixtures to be added in accordance with the invention generally also have a solubility in water which is sufficient for them also to be used in those (meth)acrylate-containing mixtures that have an aqueous as well as an organic phase.

It is surprising that mixtures of inhibitors a) and inhibitors b) have a pronounced synergistic activity for the stabilization of (meth)acrylic esters.

The stabilization of a mixture comprising (meth)acrylic esters subjected to distillation (rectification) can be simply carried out by admixing the mixture, prior to distillation (rectification), with the inhibitors to be added in accordance with the invention. Alternatively, they can be added in the feed line to the distillation (rectification) column. In both these cases, inhibitor must also be added at the top of the column in order to stabilize the column. Another possibility, of course, is to perform the entire stabilization exclusively by adding inhibitor at the column head. In the method of the invention, obviously, the inhibitors a) and inhibitors b) can be added one after the other, simultaneously or as a premix. This applies to the other inhibitors as well if present in the inhibitor mixture. The inhibitor mixture to be added in accordance with the invention may of course additionally comprise not only polymerization inhibitors a) and b) but also other polymerization inhibitors, such as phenothiazine or phenolic compounds, such as hydroquinone or its methyl ether. It is advantageous, however, if no such additional inhibitors are present. A favorable feature is that the inhibitor mixture to be used in accordance with the invention is effective even in the presence of molecular oxygen, and so the equipment containing the (meth)acrylic esters, such as distillation (rectification) columns, frequently have a through-flow of molecular oxygen or air when the method of the invention is deployed.

The activity of inhibitor mixtures is generally determined by adding the inhibitor mixture at room temperature (25° C.) to the mixture which is to be stabilized. This mixture is then heated at elevated temperature (typically in the range from 50 to 150° C.) and then a measurement is made of the time until polymerization begins (onset time). Since the polymerization is exothermic, its onset can be recognized by a temperature jump (cf. Bockstahler et al., Ind. & Eng. Chem., 50(10), 1581). The inhibitor mixtures recommended in this document for stabilizing (meth)acrylic esters can, accordingly, also be used to stabilize (meth)acrylic acid as a pure substance or constituent of mixtures.

EXAMPLES AND COMPARATIVE EXAMPLES

Example 1

50 ml of a mixture of 90.9% by weight of n-butylacrylate, 4% by weight of n-butanol, 0.8% by weight of di-n-butyl ether, 0.5% by weight of n-butyl acetate, 0.9% by weight of water and 2.9% by weight of butyl butoxypropionate were charged to a 100 ml round-bottomed flask equipped with a reflux condenser and a thermocouple, which was in turn connected to a plotter, and X ppm by weight of various polymerization inhibitors was added.

The mixture was then heated to 80° C. using a thermostated oil bath. Table 1 shows the onset times found for the various inhibitor systems.

TABLE 1

| Inhibitor | Amount of inhibitor (ppm by weight) | onset time (h) |
|---|---|---|
| — | 0 | 4 |
| Phenothiazine | 10 | 200 |
| Hydroquinone | 10 | 175 |
| N,N'-bis-sec-butyl-p-phenylene-diamine (KBPD) | 10 | 370 |
| p-Nitrosophenol | 10 | 135 |
| 2,2,6,6-Tetramethyl-1-oxyl-piperidine (TEMPO) | 10 | 760 |
| 4-Acetoxy-2,2,6,6-tetramethyl-1-oxylpiperidine (4-Acetoxy-TEMPO) | 10 | 690 |
| KBPD | 5 | 1130 |
| TEMPO | 5 | |
| KBPD | 5 | 850 |
| P-Nitrosophenol | 5 | |
| Phenothiazine | 5 | 480 |
| TEMPO | 5 | |

Example 2

An n-butyl acrylate crude ester mixture obtained by the method of direct acidic esterification of acrylic acid with n-butanol had the following composition after the acid catalyst and excess acrylic acid had been separated off:

| n-Butyl acrylate | 88% by weight |
|---|---|
| n-Butanol | 4.7% by weight |
| Di-n-butyl ether | 0.7% by weight |
| n-Butyl acetate | 0.5% by weight |
| Butyl butoxypropionate | 2.9% by weight |
| Water | 1.1% by weight |

The components boiling more readily than n-butyl acrylate were separated from this mixture in a first rectification, and the resulting bottom product was treated in a second rectification column to separate n-butyl acrylate from the components boiling less readily than n-butyl acrylate.

The feed (30 m$^3$/h) of the crude ester mixture took place onto the 49th tray of the first rectification column (60 dual-flow trays, natural circulation evaporator). The bottom temperature was 110° C. (bottom pressure=300 mbar), the column-head temperature 86° C. (column-head pressure: 150 mbar) and the return flow was 20 m$^3$/h. The amount of distillate removed at the column head was 5.6 m$^3$/h. The stabilization was effected by adding 100 ppm by weight of KBPD and 20 ppm by weight of p-nitrosophenol to the return flow (ppm by weight based on the return flow quantity). From the bottom product of the first rectification column, this product containing the heavy boilers and n-butyl acrylate, n-butyl acrylate with a purity of 99.8% by weight was separated off at the head (21.2 m$^3$/h) of a second rectification column (30 dual-flow trays, natural circulation evaporator). In the second rectification column the bottom temperature was 103° C. (bottom pressure: 150 mbar), the column-head temperature 80° C. (column-head pressure: 100 mbar) and the return flow volume ratio 1:4. The bottom liquid from the first rectification column was fed into the second rectification column at the tenth tray. To stabilize the second column, 200 ppm by weight of hydroquinone monomethyl ether (ppm by weight based on the return flow quantity) were added to this column by way of the return flow.

Even after the rectification unit had run for 25 days there was still no need to shut it down.

Comparative Example 1

The procedure of Example 2 was followed but with stabilization of the first rectification column taking place exclusively by means of 150 ppm by weight of KBPD (ppm by weight based on the return flow). The rectification unit had to be shut down after five days owing to clogging of the evaporator pipes and the formation of deposits on the column trays (of the first rectification column in each case).

Example 3

The procedure of Example 2 was followed but using 10 ppm by weight of 4-hydroxy-2,2,6,6-tetramethyl-1-oxylpiperidine instead of 20 ppm by weight of p-nitrosophenol. Even after the rectification unit had run for 25 days there was still no need to shut it down.

Example 4

The procedure of Example 2 was followed but using 20 ppm by weight of N,N'-bis(1-oxyl-2,2,6,6-tetramethylpiperidin-4-yl)-N,N'-bisformyl-1,6-diaminohexane instead of 20 ppm by weight of p-nitrosophenol. Even after the rectification unit had run for 25 days there was still no need to shut it down.

Comparative Example 2

The procedure of Example 2 was followed but with stabilization of the first rectification column taking place by means of 150 ppm by weight of hydroquinone monomethyl ether and 10 ppm by weight of 4-hydroxy-2,2,6,6-tetramethyl-1-oxylpiperidine. After six days it was necessary to shut down the rectifier owing to the formation of deposits on the column trays and in the evaporator pipes.

We claim:

1. A method of stabilizing an ester of (meth)acrylic acid against free-radical polymerization, comprising:

adding to said ester of (meth)acrylic acid a polymerization inhibitor which comprises
 a) at least one nitroxyl radical and/or at least one organic compound having at least one nitroso group; and
 b) at least one p-phenylenediamine;

wherein said ester of (meth)acrylic acid is present singly or as a constituent of a mixture which comprises no Brönsted acid whose Brönsted acid strength is greater than the Brönsted acid strength of acrylic acid.

2. A method as claimed in claim 1, wherein the mixture comprising the (meth)acrylic ester comprises <1% by weight of (meth)acrylic acid.

3. A method as claimed in claim 1, wherein the mixture comprising the (meth)acrylic ester comprises water.

4. A method as claimed in claim 1, wherein the (meth)acrylic ester is that of a $C_1$–$C_8$-alkanol.

5. A method as claimed in claim 1, wherein the polymerization inhibitors added are only inhibitors a) and inhibitors b).

* * * * *